(12) United States Patent
Koponen et al.

(10) Patent No.: US 12,390,662 B2
(45) Date of Patent: Aug. 19, 2025

(54) SYSTEM AND METHOD FOR PROTON THERAPY TREATMENT PLANNING WITH PROTON ENERGY AND SPOT OPTIMIZATION

(71) Applicant: Varian Medical Systems International AG., Cham (CH)

(72) Inventors: Timo Koponen, Espoo (FI); Perttu Niemela, Espoo (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 753 days.

(21) Appl. No.: 16/838,940

(22) Filed: Apr. 2, 2020

(65) Prior Publication Data
US 2021/0308485 A1    Oct. 7, 2021

(51) Int. Cl.
*A61N 5/10* (2006.01)
*G16H 20/40* (2018.01)

(52) U.S. Cl.
CPC ......... *A61N 5/1031* (2013.01); *A61N 5/1081* (2013.01); *G16H 20/40* (2018.01); *A61N 2005/1087* (2013.01)

(58) Field of Classification Search
CPC ............ A61N 2005/1087; A61N 5/103; A61N 5/1031; A61N 5/1043; A61N 5/1081
See application file for complete search history.

(56) References Cited

U.S. PATENT DOCUMENTS

| 4,163,901 A | 8/1979 | Azam |
| 4,914,681 A | 4/1990 | Klingenbeck et al. |

(Continued)

FOREIGN PATENT DOCUMENTS

| CN | 104001270 | 8/2014 |
| CN | 106730407 | 5/2017 |

(Continued)

OTHER PUBLICATIONS

M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/s41598-020-65819-y.

(Continued)

*Primary Examiner* — Christine H Matthews
(74) *Attorney, Agent, or Firm* — Harness, Dickey & Pierce, P.L.C.

(57) ABSTRACT

Embodiments of the present invention disclose methods and systems for proton therapy planning that includes proton energy and spot optimization that discretizes layers and spots using an optimization algorithm to produce an optimal distribution of layer energies and spots with a relatively smooth dose distribution. The treatment planning algorithms disclosed herein can freely choose the number of spots and the energy levels of the spots. In this way, each spot can be treated as its own layer and is not constrained by the requirements of other spots/layers. Thereafter, the spots defined by the algorithm can be sorted in a list according to energy levels/depth, and the spots can be grouped into blocks according to intensity and location. The blocks can be assigned energy levels based on the corresponding spots, such as an average of all the spots associated with the block. The blocks then are used as the energy layers applied by the proton therapy treatment system.

10 Claims, 6 Drawing Sheets

(56) References Cited

U.S. PATENT DOCUMENTS

| | | |
|---|---|---|
| 5,153,900 A | 10/1992 | Nomikos et al. |
| 5,267,294 A | 11/1993 | Kuroda |
| 5,550,378 A | 8/1996 | Skillicorn et al. |
| 5,610,967 A | 3/1997 | Moorman et al. |
| 5,625,663 A | 4/1997 | Swerdloff et al. |
| 5,682,412 A | 10/1997 | Skillicorn et al. |
| 5,757,885 A | 5/1998 | Yao et al. |
| 6,198,802 B1 | 3/2001 | Elliott et al. |
| 6,222,544 B1 | 4/2001 | Tarr et al. |
| 6,234,671 B1 | 5/2001 | Solomon et al. |
| 6,260,005 B1 | 7/2001 | Yang et al. |
| 6,379,380 B1 | 4/2002 | Satz |
| 6,411,675 B1 | 6/2002 | Llacer |
| 6,445,766 B1 | 9/2002 | Whitham |
| 6,504,899 B2 | 1/2003 | Pugachev et al. |
| 6,580,940 B2 | 6/2003 | Gutman |
| 6,993,112 B2 | 1/2006 | Hesse |
| 7,268,358 B2 | 9/2007 | Ma et al. |
| 7,453,983 B2 | 11/2008 | Schildkraut et al. |
| 7,515,681 B2 | 4/2009 | Ebstein |
| 7,522,706 B2 | 4/2009 | Lu et al. |
| 7,560,715 B2 | 7/2009 | Pedroni |
| 7,590,219 B2 | 9/2009 | Maurer, Jr. et al. |
| 7,616,735 B2 | 11/2009 | Maciunas et al. |
| 7,623,623 B2 | 11/2009 | Raanes et al. |
| 7,778,691 B2 | 8/2010 | Zhang et al. |
| 7,807,982 B2 | 10/2010 | Nishiuchi et al. |
| 7,831,289 B2 | 11/2010 | Riker et al. |
| 7,835,492 B1 | 11/2010 | Sahadevan |
| 7,907,699 B2 | 3/2011 | Long et al. |
| 8,284,898 B2 | 10/2012 | Ho et al. |
| 8,306,184 B2 | 11/2012 | Chang et al. |
| 8,401,148 B2 | 3/2013 | Lu et al. |
| 8,406,844 B2 | 3/2013 | Ruchala et al. |
| 8,559,596 B2 | 10/2013 | Thomson et al. |
| 8,600,003 B2 | 12/2013 | Zhou et al. |
| 8,613,694 B2 | 12/2013 | Walsh |
| 8,636,636 B2 | 1/2014 | Shukla et al. |
| 8,644,571 B1 | 2/2014 | Schulte et al. |
| 8,716,663 B2 | 5/2014 | Brusasco et al. |
| 8,836,332 B2 | 9/2014 | Shvartsman et al. |
| 8,847,179 B2 | 9/2014 | Fujitaka et al. |
| 8,903,471 B2 | 12/2014 | Heid |
| 8,917,813 B2 | 12/2014 | Maurer, Jr. |
| 8,948,341 B2 | 2/2015 | Beckman |
| 8,958,864 B2 | 2/2015 | Amies et al. |
| 8,983,573 B2 | 3/2015 | Carlone et al. |
| 8,986,186 B2 | 3/2015 | Zhang et al. |
| 8,992,404 B2 | 3/2015 | Graf et al. |
| 8,995,608 B2 | 3/2015 | Zhou et al. |
| 9,018,603 B2 | 4/2015 | Loo et al. |
| 9,033,859 B2 | 5/2015 | Fieres et al. |
| 9,079,027 B2 | 7/2015 | Agano et al. |
| 9,149,656 B2 | 10/2015 | Tanabe |
| 9,155,908 B2 | 10/2015 | Meltsner et al. |
| 9,233,260 B2 | 1/2016 | Slatkin et al. |
| 9,258,876 B2 | 2/2016 | Cheung et al. |
| 9,283,406 B2 | 3/2016 | Prieels |
| 9,308,391 B2 | 4/2016 | Liu et al. |
| 9,330,879 B2 | 5/2016 | Lewellen et al. |
| 9,333,374 B2 | 5/2016 | Iwata |
| 9,468,777 B2 | 10/2016 | Fallone et al. |
| 9,517,358 B2 | 12/2016 | Velthuis et al. |
| 9,526,918 B2 | 12/2016 | Kruip |
| 9,545,444 B2 | 1/2017 | Strober et al. |
| 9,583,302 B2 | 2/2017 | Figueroa Saavedra et al. |
| 9,636,381 B2 | 5/2017 | Basile |
| 9,636,525 B1 | 5/2017 | Sahadevan |
| 9,649,298 B2 | 5/2017 | Djonov et al. |
| 9,656,098 B2 | 5/2017 | Goer |
| 9,694,204 B2 | 7/2017 | Hardemark |
| 9,776,017 B2 | 10/2017 | Flynn et al. |
| 9,786,054 B2 | 10/2017 | Taguchi et al. |
| 9,786,093 B2 | 10/2017 | Svensson |
| 9,786,465 B2 | 10/2017 | Li et al. |
| 9,795,806 B2 | 10/2017 | Matsuzaki et al. |
| 9,801,594 B2 | 10/2017 | Boyd et al. |
| 9,844,358 B2 | 12/2017 | Wiggers et al. |
| 9,854,662 B2 | 12/2017 | Mishin |
| 9,884,206 B2 | 2/2018 | Schulte et al. |
| 9,931,522 B2 | 4/2018 | Bharadwaj et al. |
| 9,962,562 B2 | 5/2018 | Fahrig et al. |
| 9,974,977 B2 | 5/2018 | Lachaine et al. |
| 9,987,502 B1 | 6/2018 | Gattiker et al. |
| 10,007,961 B2 | 6/2018 | Grudzinski et al. |
| 10,022,564 B2 | 7/2018 | Thieme et al. |
| 10,071,264 B2 | 9/2018 | Liger |
| 10,080,912 B2 | 9/2018 | Kwak et al. |
| 10,092,774 B1 | 10/2018 | Vanderstraten et al. |
| 10,183,179 B1 | 1/2019 | Smith et al. |
| 10,188,875 B2 | 1/2019 | Kwak et al. |
| 10,206,871 B2 | 2/2019 | Lin et al. |
| 10,212,800 B2 | 2/2019 | Agustsson et al. |
| 10,232,193 B2 | 3/2019 | Iseki |
| 10,258,810 B2 | 4/2019 | Zwart et al. |
| 10,272,264 B2 | 4/2019 | Ollila et al. |
| 10,279,196 B2 | 5/2019 | West et al. |
| 10,293,184 B2 | 5/2019 | Pishdad et al. |
| 10,307,614 B2 | 6/2019 | Schnarr |
| 10,307,615 B2 | 6/2019 | Ollila et al. |
| 10,315,047 B2 | 6/2019 | Glimelius et al. |
| 10,413,755 B1 | 9/2019 | Sahadevan |
| 10,449,389 B2 | 10/2019 | Ollila et al. |
| 10,485,988 B2 | 11/2019 | Kuusela et al. |
| 10,525,285 B1 | 1/2020 | Friedman |
| 10,549,117 B2 | 2/2020 | Vanderstraten et al. |
| 10,603,514 B2 | 3/2020 | Grittani et al. |
| 10,609,806 B2 | 3/2020 | Roecken et al. |
| 10,636,609 B1 | 4/2020 | Bertsche et al. |
| 10,660,588 B2 | 5/2020 | Boyd et al. |
| 10,661,100 B2 | 5/2020 | Shen |
| 10,682,528 B2 | 6/2020 | Ansorge et al. |
| 10,702,716 B2 | 7/2020 | Heese |
| 10,758,746 B2 | 9/2020 | Kwak et al. |
| 10,870,018 B2 | 12/2020 | Bartkoski et al. |
| 2004/0227104 A1* | 11/2004 | Matsuda .............. G21K 1/08 250/492.1 |
| 2007/0287878 A1 | 12/2007 | Fantini et al. |
| 2008/0023644 A1 | 1/2008 | Pedroni |
| 2009/0063110 A1 | 3/2009 | Failla et al. |
| 2009/0287467 A1 | 11/2009 | Sparks et al. |
| 2010/0119032 A1 | 5/2010 | Yan et al. |
| 2010/0177870 A1 | 7/2010 | Nord et al. |
| 2010/0178245 A1 | 7/2010 | Arnsdorf et al. |
| 2010/0260317 A1 | 10/2010 | Chang et al. |
| 2010/0327188 A1 | 12/2010 | Bert et al. |
| 2011/0006224 A1 | 1/2011 | Maltz et al. |
| 2011/0091015 A1 | 4/2011 | Yu et al. |
| 2011/0135058 A1 | 6/2011 | Sgouros et al. |
| 2012/0076271 A1 | 3/2012 | Yan et al. |
| 2012/0157746 A1 | 6/2012 | Meltsner et al. |
| 2012/0171745 A1 | 7/2012 | Itoh |
| 2012/0197058 A1 | 8/2012 | Shukla et al. |
| 2013/0116929 A1 | 5/2013 | Carlton et al. |
| 2013/0150922 A1 | 6/2013 | Butson et al. |
| 2013/0177641 A1 | 7/2013 | Ghoroghchian |
| 2013/0231516 A1 | 9/2013 | Loo et al. |
| 2013/0267756 A1* | 10/2013 | Totake .............. A61N 5/1048 600/1 |
| 2014/0177807 A1 | 6/2014 | Lewellen et al. |
| 2014/0185776 A1 | 7/2014 | Li et al. |
| 2014/0206926 A1 | 7/2014 | van der Laarse |
| 2014/0275706 A1 | 9/2014 | Dean et al. |
| 2014/0369476 A1 | 12/2014 | Harding |
| 2015/0011817 A1 | 1/2015 | Feng |
| 2015/0202464 A1 | 7/2015 | Brand et al. |
| 2015/0265855 A1* | 9/2015 | Tachikawa .......... A61N 5/1048 600/1 |
| 2015/0306423 A1 | 10/2015 | Bharat et al. |
| 2016/0279444 A1 | 9/2016 | Schlosser |
| 2016/0310764 A1 | 10/2016 | Bharadwaj et al. |
| 2017/0189721 A1 | 7/2017 | Sumanaweera et al. |
| 2017/0203129 A1 | 7/2017 | Dessy |
| 2017/0216622 A1 | 8/2017 | Fujitaka et al. |

(56) References Cited

U.S. PATENT DOCUMENTS

| | | | |
|---|---|---|---|
| 2017/0281973 | A1 | 10/2017 | Allen et al. |
| 2018/0021594 | A1 | 1/2018 | Papp et al. |
| 2018/0043183 | A1 | 2/2018 | Sheng et al. |
| 2018/0056090 | A1 | 3/2018 | Jordan et al. |
| 2018/0099154 | A1 | 4/2018 | Prieels |
| 2018/0099155 | A1 | 4/2018 | Prieels et al. |
| 2018/0099159 | A1 | 4/2018 | Forton et al. |
| 2018/0154183 | A1 | 6/2018 | Sahadevan |
| 2018/0197303 | A1 | 7/2018 | Jordan et al. |
| 2018/0207425 | A1 | 7/2018 | Carlton et al. |
| 2018/0236268 | A1 | 8/2018 | Zwart et al. |
| 2019/0022407 | A1 | 1/2019 | Abel et al. |
| 2019/0022422 | A1 | 1/2019 | Trail et al. |
| 2019/0054315 | A1 | 2/2019 | Isola et al. |
| 2019/0070435 | A1 | 3/2019 | Joe Anto et al. |
| 2019/0168027 | A1 | 6/2019 | Smith et al. |
| 2019/0255361 | A1 | 8/2019 | Mansfield |
| 2019/0299027 | A1 | 10/2019 | Fujii et al. |
| 2019/0299029 | A1 | 10/2019 | Inoue |
| 2019/0351259 | A1 | 11/2019 | Lee et al. |
| 2020/0001118 | A1 | 1/2020 | Snider, III et al. |
| 2020/0022248 | A1 | 1/2020 | Yi et al. |
| 2020/0030633 | A1 | 1/2020 | Van Heteren et al. |
| 2020/0035438 | A1 | 1/2020 | Star-Lack et al. |
| 2020/0069818 | A1 | 3/2020 | Jaskula-Ranga et al. |
| 2020/0164224 | A1 | 5/2020 | Vanderstraten et al. |
| 2020/0178890 | A1 | 6/2020 | Otto |
| 2020/0197730 | A1 | 6/2020 | Safavi-Naeini et al. |
| 2020/0254279 | A1 | 8/2020 | Ohishi |
| 2020/0269068 | A1 | 8/2020 | Abel et al. |
| 2020/0276456 | A1 | 9/2020 | Swerdloff |
| 2020/0282234 | A1 | 9/2020 | Folkerts et al. |
| 2020/0298025 | A1* | 9/2020 | Cooley, III .......... A61N 5/1079 |

FOREIGN PATENT DOCUMENTS

| | | |
|---|---|---|
| CN | 107362464 | 11/2017 |
| CN | 109966662 | 7/2019 |
| CN | 111481840 | 8/2020 |
| CN | 111481841 | 8/2020 |
| EA | 010207 | 6/2008 |
| EP | 0979656 | 2/2000 |
| EP | 2510978 | 10/2012 |
| EP | 3178522 | 6/2017 |
| EP | 3338858 | 6/2018 |
| EP | 3384961 | 10/2018 |
| EP | 3421087 | 1/2019 |
| EP | 3453427 | 3/2019 |
| EP | 3586920 | 1/2020 |
| JP | 2617283 | 6/1997 |
| JP | 2019097969 | 6/2019 |
| WO | 2007017177 | 2/2007 |
| WO | 2010018476 | 2/2010 |
| WO | 2013081218 | 6/2013 |
| WO | 2013133936 | 9/2013 |
| WO | 2014139493 | 9/2014 |
| WO | 2015038832 | 3/2015 |
| WO | 2015102680 | 7/2015 |
| WO | 2016122957 | 8/2016 |
| WO | 2017156316 | 9/2017 |
| WO | 2017156419 | 9/2017 |
| WO | 2017174643 | 10/2017 |
| WO | 2018137772 | 8/2018 |
| WO | 2018152302 | 8/2018 |
| WO | 2019097250 | 5/2019 |
| WO | 2019103983 | 5/2019 |
| WO | 2019164835 | 8/2019 |
| WO | 2019166702 | 9/2019 |
| WO | 2019185378 | 10/2019 |
| WO | 2019222436 | 11/2019 |
| WO | 2020018904 | 1/2020 |
| WO | 2020064832 | 4/2020 |
| WO | 2020107121 | 6/2020 |
| WO | 2020159360 | 8/2020 |

OTHER PUBLICATIONS

Ibrahim Oraiqat et al., "An Ionizing Radiation Acoustic Imaging (iRAI) Technique for Real-Time Dosimetric Measurements for FLASH Radiotherapy," Medical Physics, vol. 47, Issue 10, Oct. 2020, pp. 5090-5101, First published: Jun. 27, 2020, https://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHROcDovL2FwaS5lbHNldmllci5jb20vY29udGVudC9hcnRpY2xlL3BpaS9zMDE2NzgxNDAxNjMwMTcyNA==.pdf.

Susanne Auer et al., "Survival of tumor cells after proton irradiation with ultra-high dose rates," Radiation Oncology 2011, 6:139, Published Oct. 18, 2011, DOI: https://doi.org/10.1186/1748-717X-6-139.

Cynthia E. Keen, "Clinical linear accelerator delivers FLASH radiotherapy," Physics World, Apr. 23, 2019, IOP Publishing Ltd, https://physicsworld.com/a/clinical-linear-accelerator-delivers-flash-radiotherapy/.

Fan et al., "Emission guided radiation therapy for lung and prostate cancers: A feasibility study on a digital patient," Med Phys. Nov. 2012; 39(11): 7140-7152. Published online Nov. 5, 2012. https://www.ncbi.nlm.nih.gov/pmc/articles/PMC3505203/ doi: 10.1118/1.4761951.

Favaudon et al., "Ultrahigh dose-rate, "flash" irradiation minimizes the side-effects of radiotherapy," Cancer / Radiotherapy, vol. 19, Issues 6-7 , Oct. 2015 , pp. 526-531, Available online Aug. 12, 2015, https://doi.org/10.1016/j.canrad.2015.04.006.

O. Zlobinskaya et al., "The Effects of Ultra-High Dose Rate Proton Irradiation on Growth Delay in the Treatment of Human Tumor Xenografts in Nude Mice," Radiation Research, 181(2):177-183. Published Feb. 13, 2014, DOI: http://dx.doi.org/10.1667/RR13464.1.

Bjorn Zackrisson, "Biological Effects Of High Energy Radiation And Ultra High Dose Rates," UMEA University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369, Available online May 22, 2017, doi: 10.1016/j.radonc.2017.05.003.

BW Loo et al., "Delivery of Ultra-Rapid Flash Radiation Therapy and Demonstration of Normal Tissue Sparing After Abdominal Irradiation of Mice," International Journal of Radiation Oncology, Biology, Physics, vol. 98, Issue 2, p. E16, Supplement: S Meeting Abstract: P003, Published: Jun. 1, 2017, DOI: https://doi.org/10.1016/j.ijrobp.2017.02.101.

Bhanu Prasad Venkatesulu et al., "Ultra high dose rate (35 Gy/sec) radiation does not spare the normal tissue In cardiac and splenic models of lymphopenia and gastrointestinal syndrome," Sci Rep 9, 17180 (2019), Published Nov. 20, 2019, DOI: https://doi.org/10.1038/s41598-019-53562-y.

P. Montay-Gruel et al., "Long-term neurocognitive benefits of FLASH radiotherapy driven by reduced reactive oxygen species," PNAS May 28, 2019, vol. 116, No. 22, pp. 10943-10951; first published May 16, 2019, https://doi.org/10.1073/pnas.1901777116.

Peter G. Maxim et al., "FLASH radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp.13685.

Andrei Pugachev et al., "Pseudo beam's-eye-view as applied to beam orientation selection in intensity-modulated radiation therapy," Int. J. Radiation Oncology Biol. Phys., vol. 51, Issue 5, p. 1361-1370, Dec. 1, 2001, DOI: https://doi.org/10.1016/S0360-3016(01)01736-9.

Xiaodong Zhang et al., "Intensity-Modulated Proton Therapy Reduces the Dose to Normal Tissue Compared With Intensity-Modulated (56) References Cited

OTHER PUBLICATIONS

Radiation Therapy or Passive Scattering Proton Therapy and Enables Individualized Radical Radiotherapy for Extensive Stage IIIB Non-Small-Cell Lung Cancer: A Virtual Clinical Study," Int. J. Radiation Oncology Biol. Phys., vol. 77, No. 2, pp. 357-366, 2010, Available online Aug. 5, 2009, DOI: https://doi.org/10.1016/j.ijrobp.2009.04.028.

A. J. Lomax et al., "Intensity modulated proton therapy: A clinical example," Medical Physics, vol. 28, Issue 3, Mar. 2001, pp. 317-324, First published: Mar. 9, 2001, https://doi.org/10.1118/1.1350587.

Lamberto Widesott et al., "Intensity-Modulated Proton Therapy Versus Helical Tomotherapy in Nasopharynx Cancer: Planning Comparison and NTCP Evaluation," Int. J. Radiation Oncology Biol. Phys., vol. 72, No. 2, pp. 589-596, Oct. 1, 2008, Available online Sep. 13, 2008, DOI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.

Damien C. Weber et al., "Radiation therapy planning with photons and protons for early and advanced breast cancer: an overview," Radiat Oncol. 2006; 1: 22. Published online Jul. 20, 2006, doi: 10.1186/1748-717X-1-22.

RaySearch Laboratories, "Leading the way in cancer treatment, Annual Report 2013," RaySearch Laboratories (publ), Stockholm, Sweden, 94 pages, Apr. 2014, https://www.raysearchlabs.com/siteassets/about-overview/media-center/wp-re-ev-n-pdfs/brochures/raysearch-ar-2013-eng.pdf.

Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fredrik_light.pdf.

Chang-Ming Charlie Ma, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.

Alterego-Admin, "Conventional Radiation Therapy May Not Protect Healthy Brain Cells," International Neuropsychiatric Association—INA, Oct. 10, 2019, https://inawebsite.org/conventional-radiation-therapy-may-not-protect-healthy-brain-cells/.

Schell Stefan et al., "Advanced treatment planning methods for efficient radiation therapy with laser accelarated proton and ion beams", Medical Physics, AIP, Melville, NY, US, vol. 37, No. 10, Sep. 20, 2010 (Sep. 20, 2010), pp. 5330-5340.

Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10.1088/0031-9155/60/8/R155.

S E McGowan et al., "Treatment planning optimisation in proton therapy," Br J Radiol, 2013, 86, 20120288, The British Institute of Radiology, 12 pages, DOI: 10.1259.bjr.20120288.

Steven Van De Water et al., "Towards FLASH proton therapy: the impact of treatment planning and machine characteristics on achievable dose rates," Acta Oncologica, Jun. 26, 2019, vol. 58, No. 10, p. 1462-1469, Taylor & Francis Group, DOI: 10.1080/0284186X.2019.1627416.

J. Groen, "FLASH optimisation in clinical IMPT treatment planning," MSc Thesis, Jul. 1, 2020, Erasmus University Medical Center, department of radiotherapy, Delft University of Technology, 72 pages.

Muhammad Ramish Ashraf et al., "Dosimetry for FLASH Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate FLASH Irradiation of Small Animals Using a Clinical Linear Accelerator," International Journal of Radiation Oncology, Biology, Physics, vol. 97, No. 1, Sep. 2016, pp. 195-203.

Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.

P-H Mackeprang et al., "Assessing dose rate distributions in VMAT plans" (Accepted Version), Accepted Version: https://boris.unibe.ch/92814/8/dose_rate_project_revised_submit.pdf Published Version: 2016, Physics in medicine and biology, 61(8), pp. 3208-3221. Institute of Physics Publishing IOP, published Mar. 29, 2016, https://boris.unibe.ch/92814/.

Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, p. 59-69, Published by Elsevier Inc., Oct. 15, 2019.

Alexei Trofimov et al., "Optimization of Beam Parameters and Treatment Planning for Intensity Modulated Proton Therapy," Technology in Cancer Research & Treatment, vol. 2, No. 5, Oct. 2003, p. 437-444, Adenine Press.

Vladimir Anferov, "Scan pattern optimization for uniform proton beam scanning," Medical Physics, vol. 36, Issue 8, Aug. 2009, pp. 3560-3567, First published: Jul. 2, 2009.

Ryosuke Kohno et al., "Development of Continuous Line Scanning System Prototype for Proton Beam Therapy," International Journal of Particle Therapy, Jul. 11, 2017, vol. 3, Issue 4, p. 429-438, DOI: 10.14338/IJPT-16-00017.1.

Wenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019 https://www.ncbi.nlm.nih.gov/pmc/articles/PMC5904040/ Published in final edited form as: Med Phys. Apr. 2018; 45(4): 1338-1350. Published online Mar. 1, 2018. doi: 10.1002/mp.12788 Accepted manuscript online: Feb. 2, 2018.

Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.

Simeon Nill et al., "Inverse planning of intensity modulated proton therapy," Zeitschrift fur Medizinische Physik, vol. 14, Issue 1, 2004, pp. 35-40, https://doi.org/10.1078/0939-3889-00198.

A. Lomax, "Intensity modulation methods for proton radiotherapy," Physics in Medicine & Biology, Jan. 1999, vol. 44, No. 1, pp. 185-205, doi: 10.1088/0031-9155/44/1/014.

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.

Harald Paganetti, "Proton Beam Therapy," Jan. 2017, Physics World Discovery, IOP Publishing Ltd, Bristol, UK, 34 pages, DOI: 10.1088/978-0-7503-1370-4.

Shinichi Shimizu et al., "A Proton Beam Therapy System Dedicated to Spot-Scanning Increases Accuracy with Moving Tumors by Real-Time Imaging and Gating and Reduces Equipment Size," PLoS One, Apr. 18, 2014, vol. 9, Issue 4, e94971, https://doi.org/10.1371/journal.pone.0094971.

Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.

Ion Beam Applications SA, "Netherlands Proton Therapy Center Delivers First Clinical Flash Irradiation," Imaging Technology News, May 2, 2019, Wainscot Media, https://www.itnonline.com/content/netherlands-proton-therapy-center-delivers-first-clinical-flash-irradiation.

R. M. De Kruijff, "FLASH radiotherapy: ultra-high dose rates to spare healthy tissue," International Journal of Radiation Biology,

(56) References Cited

OTHER PUBLICATIONS 2020, vol. 96, No. 4, pp. 419-423, published online: Dec. 19, 2019, https://doi.org/10.1080/09553002.2020.1704912.

Mevion Medical Systems, "Focus On The Future: Flash Therapy," Press Releases, Sep. 16, 2019, https://www.mevion.com/newsroom/press-releases/focus-future-flash-therapy.

Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019.01563.

David P. Gierga, "Is Flash Radiotherapy coming?", International Organization for Medical Physics, 2020, https://www.iomp.org/iomp-news2-flash-radiotherapy/.

Abdullah Muhammad Zakaria et al., "Ultra-High Dose-Rate, Pulsed (FLASH) Radiotherapy with Carbon Ions: Generation of Early, Transient, Highly Oxygenated Conditions in the Tumor Environment," Radiation Research, Dec. 1, 2020, vol. 194, Issue 6, pp. 587-593, Radiation Research Society, Published: Aug. 27, 2020, doi: https://doi.org/10.1667/RADE-19-00015.1.

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.

Ivana Dokic et al., "Next generation multi-scale biophysical characterization of high precision cancer particle radiotherapy using clinical proton, helium-, carbon- and oxygen ion beams," Oncotarget, Aug. 30, 2016, vol. 7, No. 35, pp. 56676-56689, published online: Aug. 1, 2016, doi: 10.18632/oncotarget.10996.

Aetna Inc., "Proton Beam, Neutron Beam, and Carbon Ion Radiotherapy," 2020, No. 0270, http://www.aetna.com/cpb/medical/data/200_299/0270.html.

Nicholas W. Colangelo et al., "The Importance and Clinical Implications of FLASH Ultra-High Dose-Rate Studies for Proton and Heavy Ion Radiotherapy," Radiat Res. Author manuscript; available in PMC Jan. 1, 2021. https://www.ncbi.nlm.nih.gov/pmc/articles/PMC6949397/ Published in final edited form as: Radiat Res. Jan. 2020; 193(1): 1-4. Published online Oct. 28, 2019. doi: 10.1667/RR15537.1.

Vincent Favaudon et al., "Ultrahigh dose-rate FLASH irradiation increases the differential response between normal and tumor tissue in mice," Science Translational Medicine, Jul. 16, 2014, vol. 6, Issue 245, 245ra93, American Association for the Advancement of Science, DOI: 10.1126/scitranslmed.3008973.

"FlashRad: Ultra-high dose-rate FLASH radiotherapy to minimize the complications of radiotherapy," 2014, https://siric.curie.fr/sites/default/files/atoms/files/flashrad.pdf.

Tami Freeman, "FLASH radiotherapy: from preclinical promise to the first human treatment," Physics World, Aug. 6, 2019, IOP Publishing Ltd, https://physicsworld.com/a/flash-radiotherapy-from-preclinical-promise-to-the-first-human-treatment/.

Intraop Medical, Inc., "IntraOp and Lausanne University Hospital Announce Collaboration in FLASH radiotherapy," Jun. 18, 2020, https://intraop.com/news-events/lausanne-university-flash-radiotherapy-collaboration/.

M.-C. Vozenin et al., "Biological Benefits of Ultra-high Dose Rate FLASH Radiotherapy: Sleeping Beauty Awoken," Clin Oncol (R Coll Radiol). Author manuscript; available in PMC Nov. 12, 2019. https://www.ncbi.nlm.nih.gov/pmc/articles/PMC6850216/ Published in final edited form as: Clin Oncol (R Coll Radiol). Jul. 2019; 31(7): 407-415. Published online Apr. 19, 2019. doi: 10.1016/j.clon.2019.04.001.

Efstathios Kamperis et al., "A FLASH back to radiotherapy's past and then fast forward to the future," J Cancer Prev Curr Res. 2019; 10(6): 142-144. published Nov. 13, 2019, DOI: 10.15406/jcpcr.2019.10.00407.

P. Symonds et al., "FLASH Radiotherapy: The Next Technological Advance in Radiation Therapy?", Clinical Oncology, vol. 31, Issue 7, p. 405-406, Jul. 1, 2019, The Royal College of Radiologists, Published by Elsevier Ltd., DOI: https://doi.org/10.1016/j.clon.2019.05.011.

Swati Girdhani et al., "Abstract LB-280: FLASH: A novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. LB-280, American Association for Cancer Research, DOI: https://doi.org/10.1158/1538-7445.AM2019-LB-280.

Bazalova-Carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine, doi: 10.1002/mp.13858. Epub Oct. 23, 2019. PMID: 31600830.

Manuela Buonanno et al., "Biological effects in normal cells exposed to FLASH dose rate protons," Radiother Oncol. Author manuscript; available in PMC Oct. 1, 2020. https://www.ncbi.nlm.nih.gov/pmc/articles/PMC6728238/ Published in final edited form as: Radiother Oncol. Oct. 2019; 139: 51-55. Published online Mar. 5, 2019. doi: 10.1016/j.radonc.2019.02.009.

N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement, S164-S165, Sep. 1, 2019, Mini Oral Sessions, DOI: https://doi.org/10.1016/j.ijrobp.2019.06.187.

Inserm Press Office, "Radiotherapy 'flashes' to reduce side effects," Press Release, Jul. 16, 2014, https://presse.inserm.fr/en/radiotherapy-flashes-to-reduce-side-effects/13394/.

Eric S. Diffenderfer et al., "Design, Implementation, and in Vivo Validation of a Novel Proton FLASH Radiation Therapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.

Valerie Devillaine, "Radiotherapy and Radiation Biology," Institut Curie, Apr. 21, 2017, https://institut-curie.org/page/radiotherapy-and-radiation-biology.

Imaging Technology News, "ProNova and medPhoton to Offer Next Generation Beam Delivery, Advanced Imaging for Proton Therapy," Oct. 6, 2014, Wainscot Media, Link: https://www.itnonline.com/content/pronova-and-medphoton-offer-next-generation-beam-delivery-advanced-imaging-proton-therapy.

Oncolink Team, "Radiation Therapy: Which type is right for me?", OncoLink Penn Medicine, last reviewed Mar. 3, 2020, Trustees of the University of Pennsylvania, https://www.oncolink.org/cancer-treatment/radiation/introduction-to-radiation-therapy/radiation-therapy-which-type-is-right-for-me.

Marco Durante et al., "Faster and safer? FLASH ultra-high dose rate in radiotherapy," Br J Radiol 2018; 91(1082):20170628, British Institute of Radiology, Published Online: Dec. 15, 2017, https://doi.org/10.1259/bjr.20170628.

John R. Fischer, "PMB launches FLASH radiotherapy system for use in clinical trials," HealthCare Business News, Jun. 29, 2020, DOTmed.com, Inc., https://www.dotmed.com/news/story/51662.

Marie-Catherine Vozenin et al., "The advantage of FLASH radiotherapy confirmed in mini-pig and cat-cancer patients," Clinical Cancer Research, Author Manuscript Published OnlineFirst Jun. 6, 2018, https://clincancerres.aacrjournals.org/content/clincanres/early/2018/06/06/1078-0432.CCR-17-3375.full.pdf.

\* cited by examiner

SYSTEM AND METHOD FOR PROTON THERAPY TREATMENT PLANNING WITH PROTON ENERGY AND SPOT OPTIMIZATION

FIELD

Embodiments of the present invention generally relate to the field of radiotherapy treatment and systems for same. More specifically, embodiments of the present invention relate to systems and methods for proton therapy treatment planning.

BACKGROUND

Particle therapy with protons or other ions is a type of radiotherapy that uses an external beam to provide targeted ionizing radiation to a tumor. Protons or other positively charged ions are sent to an accelerator to bring the particles' energy to a predetermined value. The protons or other ions then move through a beam-transport system, where magnets are used to shape, focus and/or direct the proton beam or other ion beam as necessary.

Standard radiation therapy systems deposit energy in "spots" along the path of the beam to a target tumor. However, the reach of the energy also extends beyond the target tumor, and may deliver radiation to healthy tissue around the tumor site. This excess radiation may damage normal tissue or organs near the target area. Moreover, the selection of specific energies and the number of spots are decided based only on patient geometry and hardware constraints. The subsequent optimization to achieve the dosimetric criteria for treatment is traditionally performed only on spot intensities, which can produce less than optimal results. It is appreciated that the term spot intensity is used here as a synonym to monitor unit count, e.g., the intensity is a relative quantity proportional to the number of protons per spot, as delivered by the treatment machine.

Radiation treatment plans can be optimized according to given dose volume objectives for target volume and organs at risk and according to plan robustness using commercially available treatment planning systems. Dose distributions are calculated using beam characteristics and a machine specific dose calibration. However, machine or system limitations can lead to a translation of an aimed dose distribution into machine/treatment delivery system parameters that may generate an unacceptable treatment plan. Additionally, the generated treatment plan may not use the full system/machine capability to make use of the system in the most efficient and reliable manner. The treatment plan can be optimized for efficiency and may employ a trial-and-error modification of several complex associated plan parameters (e.g., energy layer distance, spot size or spot spacing) required for multi-directional optimization. Even if an optimized treatment plan finally passes the criteria for plan quality and treatment delivery time, the manual trial and-error-process is time consuming and may not be able to achieve the optimal delivery efficiency.

More specifically, particle therapy planning using existing techniques is constrained by the delivery of doses in discrete, predetermined increments. For example, to deliver dose to a 3D volume, multiple discrete beam energies are required and further, the dose with energy must be delivered in discrete spots. Traditionally, the discretization scheme, including the selection of specific energies, the number of spots, and their locations, are decided based on patient geometry and hardware constraints, and the treatment planning optimization is limited by these constraints. Rather, the subsequent optimization to achieve the dosimetric criteria for treatment is traditionally performed only on spot intensities. Because there is a lower limit for the intensity per each spot, the layers used to deliver the dose will only include a relatively low number of spots. This often disadvantageously results in an uneven dose distribution, which is considered clinically suboptimal.

Because layer energies are pre-determined by existing treatment planning solutions, there is nothing the optimization algorithm can do to resolve these constraints. Therefore, what is needed is an approach to particle therapy treatment that discretizes layers and spots using an optimization algorithm without the existing constraints, that produces an optimal distribution of layer energies and spots with a smoother (e.g., more even) dose distribution, and that can advantageously produce fewer layers and potentially fewer spots, thereby reducing the time taken to treat a patient. Therefore, what is needed is an approach to particle therapy treatment that addresses these issues.

SUMMARY

More specifically, what is needed is an approach to particle therapy treatment that discretizes layers and spots using an optimization algorithm without the existing constraints, that produces an optimal distribution of layer energies and spots with a smoother (e.g., more even) dose distribution, and that can advantageously produce fewer layers and potentially fewer spots, thereby reducing the time required to treat a patient. Accordingly, methods and systems for proton therapy planning that include proton energy and spot optimization that discretizes layers and spots using an optimization algorithm to produce an optimal distribution of layer energies and spots with a relatively smooth dose distribution are disclosed herein. Embodiments of the present invention can thereby produce fewer layers and potentially fewer spots, thereby advantageously reducing the time required to treat a patient.

According to one embodiment, a system for proton therapy treatment is disclosed. The system includes a gantry including a nozzle emitting a controllable proton beam, a proton therapy treatment system that controls the gantry according to a treatment plan, and a treatment planning system including a memory, and a processor operable to perform a method for generating the treatment plan. The method includes receiving treatment planning parameters, determining a number of spots and energy levels of the spots according to the treatment planning parameters, calculating intensities for the spots according to the energy levels, discretizing the spots into a plurality of blocks according to a location of the spots and the intensities of the spots, wherein the treatment plan comprises the blocks, and where the block represent an energy layer applied by the gantry, and outputting the treatment plan.

According to some embodiments, the method includes treating a patient using the gantry according to the treatment plan.

According to some embodiments, the discretizing the spots into a plurality of blocks is performed iteratively until a clinical goal is achieved.

According to some embodiments, the method includes determining a plurality of angles for performing proton therapy treatment and where the determining a number of spots and energy levels of the spots is further based on the plurality of angles.

According to some embodiments, the method includes receiving the number of layers as user input, where the determining a number of spots and energy levels of the spots is further based on the number of layers.

According to some embodiments, the method includes sorting the spots according to depth before discretizing the spots.

According to some embodiments, the method includes sorting the spots according to energy level before discretizing the spots.

According to some embodiments, the energy layers have a fixed width.

According to some embodiments, the method includes the energy layers have a fixed intensity.

According to another embodiment, a method for proton therapy treatment is disclosed. The method includes receiving treatment planning parameters, determining a number of spots and energy levels of the spots according to the treatment planning parameters, sorting the spots based on a depth of a respective spot, calculating intensities for the spots according to the energy levels, discretizing the spots into a plurality of blocks according to a location of the spots and the intensities of the spots, where each block represents an energy layer applied by the gantry, and outputting the treatment plan, wherein the treatment plan comprises the blocks.

According to a different embodiment, a non-transitory computer-readable storage medium having embedded therein program instructions, which when executed by one or more processors of a device, causes the device to execute a method for proton therapy treatment. The method includes receiving treatment planning parameters, determining a number of spots and energy levels of the spots according to the treatment planning parameters, sorting the spots based on a depth of a respective spot, calculating intensities for the spots according to the energy levels, discretizing the spots into a plurality of blocks according to a location of the spots and the intensities of the spots, where each block represents an energy layer applied by the gantry, and outputting the treatment plan, wherein the treatment plan comprises the blocks.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, components, and circuits have not been described in detail as not to unnecessarily obscure aspects and features of the subject matter.

Portions of the detailed description that follows are presented and discussed in terms of a method. Although steps and sequencing thereof are disclosed in a figure herein describing the operations of this method, such steps and sequencing are exemplary. Embodiments are well suited to performing various other steps or variations of the steps recited in the flowchart (e.g., FIG. 5) of the figures herein, and in a sequence other than that depicted and described herein.

Some portions of the detailed description are presented in terms of procedures, steps, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "generating," "writing," "including," "storing," "transmitting," "traversing," "associating," "identifying," "optimizing" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Some embodiments may be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Energy and Spot Optimization for Proton Therapy Treatment

The following description is presented to enable a person skilled in the art to make and use the embodiments of this invention; it is presented in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present invention is not limited to the embodiments shown, but is to be accorded the widest scope consistent with the principles and features disclosed herein.

Methods and systems for proton therapy planning including proton energy and spot optimization that discretizes layers and spots using an optimization process are described herein. The optimization process produces an optimal distribution of layer energies and spots with a relatively smooth dose distribution, and can freely choose the number of spots and the energy levels of the spots. In this way, each spot can be treated as its own layer and is not constrained by the requirements of other spots/layers. Thereafter, the spots defined by the process can be sorted into a list according to energy levels/depths, and the spots can be grouped into blocks. The blocks can be assigned energy levels based on the corresponding spots, for example, using an average of all of the spots associated with the block. The blocks are then used to define the energy levels applied by the proton therapy treatment system.

Embodiments of the present invention can thereby produce fewer layers and potentially fewer spots, thereby advantageously reducing the time required to treat a patient. The optimization processes, e.g., algorithms, described herein can split individual spots among different layers to avoid creating spots that are below the minimum energy threshold deliverable by the treatment system. The spots can be divided into layers such that the layers receive substantially equal intensities. For example, the spots can be divided into layers so that each layer receives a substantially equal number of protons delivered by the proton therapy treatment system. In general, a treatment plan that is optimized using fewer layers leads to a faster delivery time. On the other hand, embodiments of the present invention can also optimize proton treatment plans for accuracy by using more spots and/or layers to better fit the target volume. The spots can be distributed at fixed intervals (e.g., 3 mm spacing) or distributed based on variations such as beam energy and/or beam range. In all cases, the general principle holds that the intensity of a layer is the sum of the intensities of all spots on a given layer.

Figure 1:
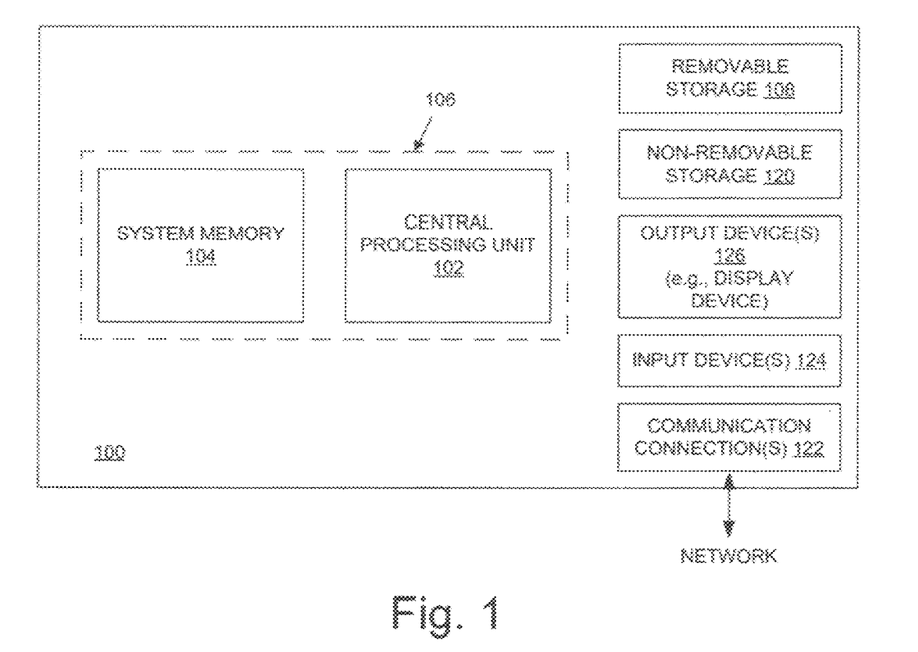
FIG. 1 shows a block diagram of an example of a computing system upon which the embodiments described herein may be implemented.

FIG. 1 shows a block diagram of an example of a computing system 100 upon which the embodiments described herein may be implemented. In a basic configuration, the system 100 includes at least one processing unit 102 and a memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 of FIG. 1 also includes input device(s) 124 such as keyboard, mouse, pen, voice input device, touch input device, etc. Output device(s) 126 such as a display device, speakers, printer, etc., are also included.

In the example of FIG. 1, the memory 104 includes computer-readable instructions, data structures, program modules, and the like. Depending on how it is to be used, the system 100—by executing the appropriate instructions or the like—can be used to implement a planning system used that discretizes layers and spots using an optimization algorithm (comprising computer readable instructions) to produce an optimal distribution of layer energies and spots with a relatively smooth dose distribution. The treatment planning algorithms executed by CPU 102 can freely choose the number of spots and the energy levels of the spots so that each spot can be treated as its own layer unconstrained by the requirements of other spots/layers. Thereafter, the spots defined by the algorithm can be sorted in a list according to energy levels/depth using CPU 102, and the spots can be grouped into blocks. The blocks can be assigned energy levels based on corresponding spots, for example, using an average of all spots associated with the block. More generally, system 100 can be used to generate and/or optimize proton therapy treatment plans in accordance with the present invention.

Figure 2:
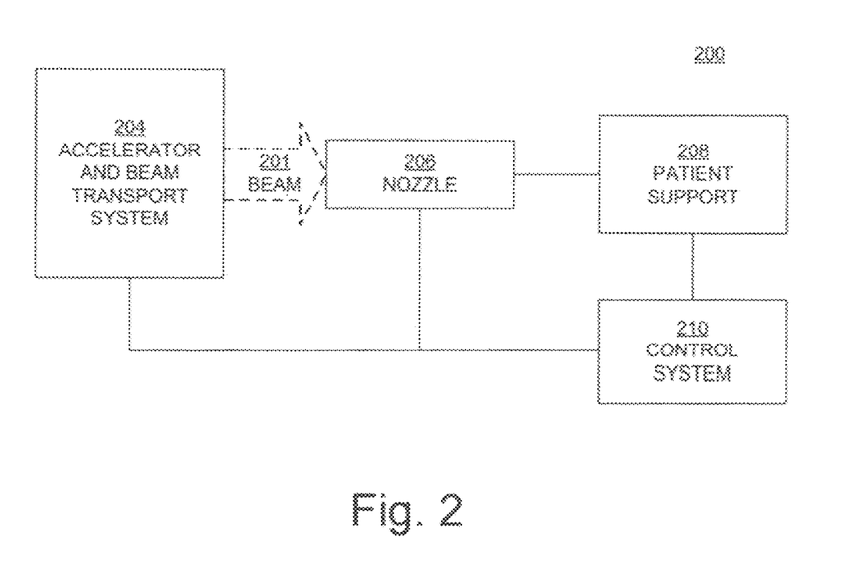
FIG. 2 is a block diagram showing selected components of a radiation treatment system upon which embodiments according to the present invention can be implemented.

FIG. 2 is a block diagram showing selected components of a radiation treatment system 200 upon which embodiments according to the present invention can be implemented. In the example of FIG. 2, the system 200 includes an accelerator and beam transport system 204 that generate and/or accelerate a beam 201. Embodiments according to the invention can generate and deliver beams of various types including, for instance, proton beams, electron beams, neutron beams, photon beams, ion beams, or atomic nuclei beams (e.g., using elements such as carbon, helium, or lithium) and the like. The operations and parameters of the accelerator and beam transport system 204 are controlled so that the intensity, energy, size, and/or shape of the beam are dynamically modulated or controlled during treatment of a patient according to an optimized radiation treatment plan produced by system 100 as discussed above.

A recent radiobiology study has demonstrated the effectiveness of delivering an entire, relatively high therapeutic radiation dose to a target within a single, short period of time. This type of treatment is referred to generally herein as FLASH radiation therapy (FLASH RT). Evidence to date suggests that FLASH RT advantageously spares normal, healthy tissue from damage when that tissue is exposed to only a single irradiation for only a very short period of time. For FLASH RT, the accelerator and beam transport system 204 can generate beams that can deliver at least four (4) grays (Gy) in less than one second, and may deliver as much as 20 Gy or 50 Gy, or more, in less than one second. The control system 210 can execute a treatment plan for FLASH RT, and the plan can be generated or optimized by system 100 executing an optimization algorithm in accordance with embodiments of the present invention.

The nozzle 206 is used to aim the beam toward various locations (a target) within a patient supported on the patient support device 208 (e.g., a chair, couch, or table) located in a treatment room. A target may be an organ, a portion of an organ (e.g., a volume or region within the organ), a tumor, diseased tissue, or a patient outline, for instance.

The nozzle 206 may be mounted on or may be a part of a gantry (FIG. 3) that can be moved relative to the patient support device 208, which may also be moveable. In embodiments, the accelerator and beam transport system 204 are also mounted on, or are a part of, the gantry structure; in another embodiment, the accelerator and beam transport system are separate from (but in communication with) the gantry structure.

The control system 210 of FIG. 2 receives and implements a prescribed treatment plan generated and/or optimized according to embodiments of the present invention. In embodiments, the control system 210 includes a computing system having a processor, memory, an input device (e.g., a keyboard), and perhaps optionally a display; the system 100 of FIG. 1 is an example of such a platform for the control system 210. The control system 210 can receive data regarding the operation of the system 200. The control system 210 can control parameters of the accelerator and beam transport system 204, nozzle 206, and patient support device 208, including parameters such as the energy, intensity, size, and/or shape of the beam, direction of the nozzle, and position of the patient support device (and the patient) relative to the nozzle, according to data the control system 210 receives and according to the radiation treatment plan.

Figure 3:
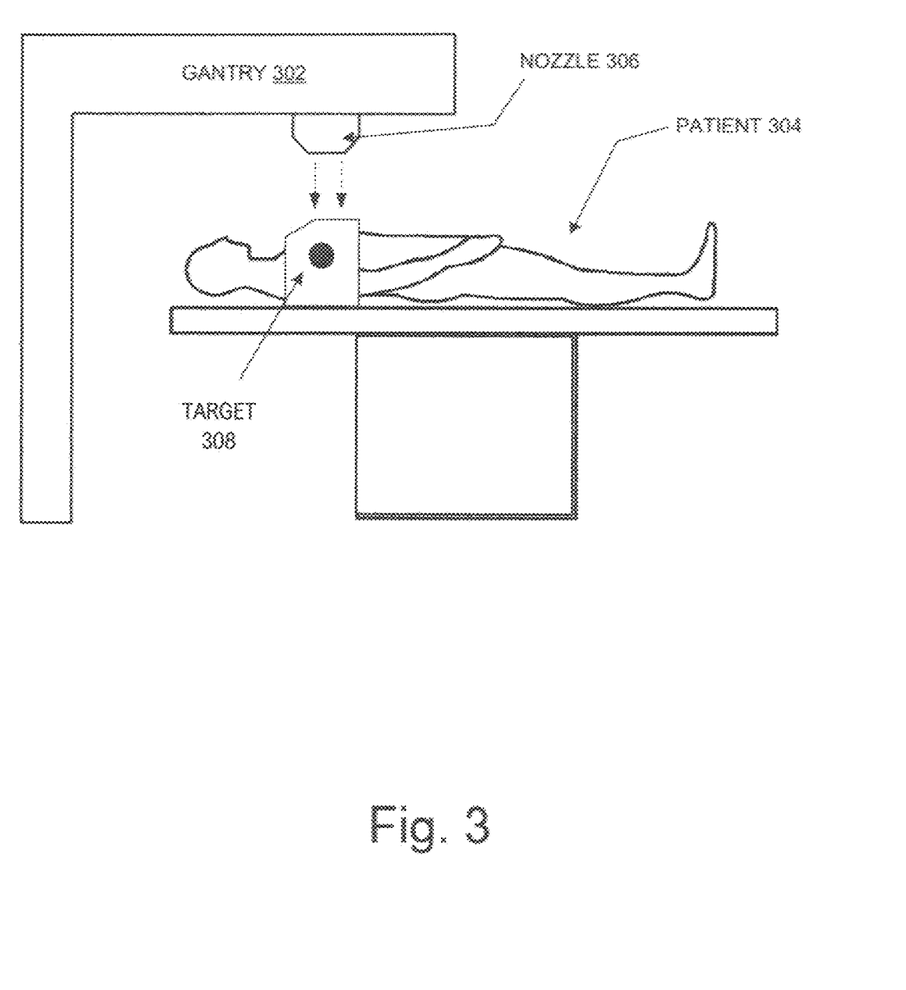
FIG. 3 illustrates elements of a radiation treatment system in accordance with embodiments according to the invention.

FIG. 3 illustrates elements of a radiation treatment system 300 for treating a patient 304 in embodiments according to the present invention. The system 300 is an example of an implementation of the radiation treatment system 200 of FIG. 2, for example. In embodiments, the gantry 302 and nozzle 306 can be moved up and down the length of the patient 304 and/or around the patient, and the gantry and nozzle can move independently of one another. While the patient 304 is supine in the example of FIG. 3, the invention is not so limited to this orientation. For example, the patient 304 can instead be seated in a chair or standing. The gantry 302 can be controlled by a treatment system using an optimized treatment plan generated according to embodiments of the present invention.

Figure 4:
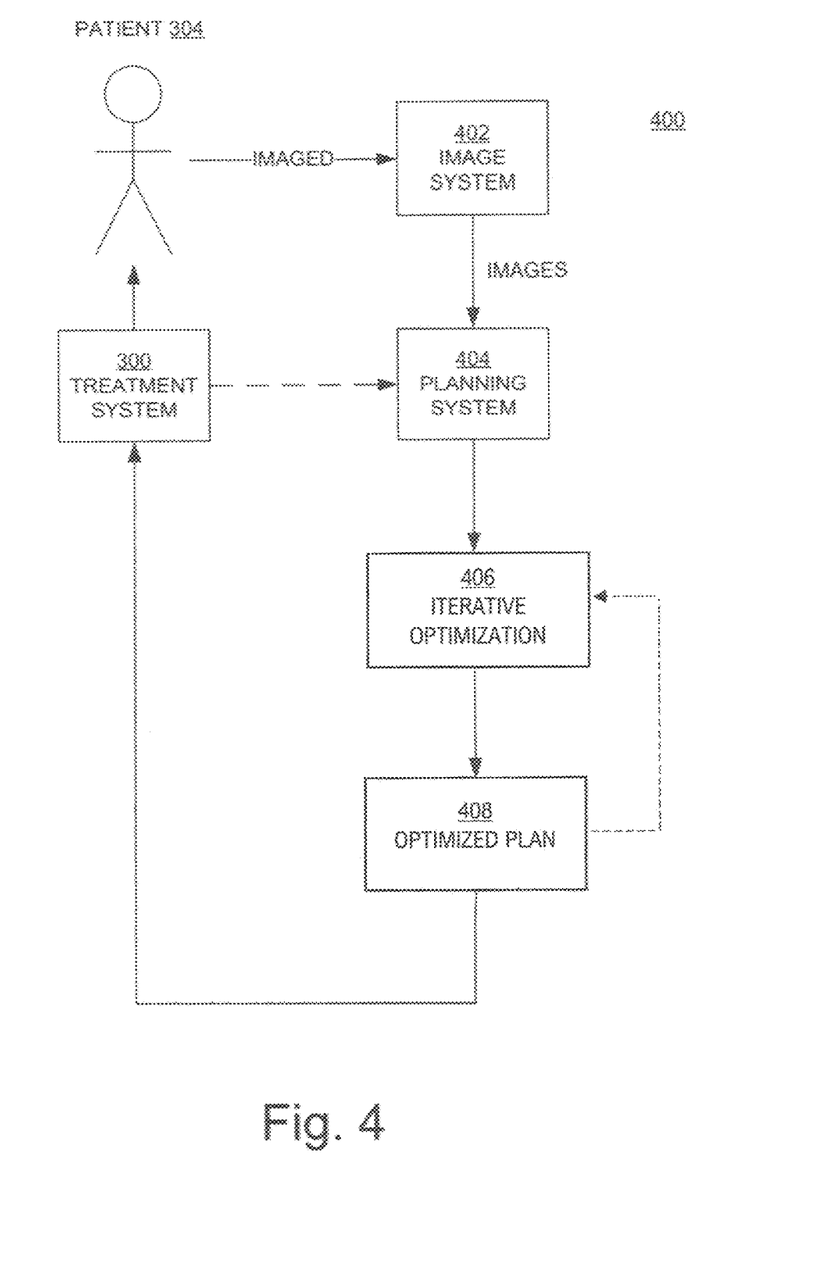
FIG. 4 is a block diagram illustrating components in a process for creating an optimized proton therapy treatment plan in embodiments according to the present invention.

With regard to FIG. 4, an exemplary proton therapy system 400 for imaging and treating a patient 304 is depicted according to embodiments of the present invention. In the example of FIG. 4, patient 304 is imaged using an image system 402 that uses, for example, x-rays, magnetic resonance imaging (MRI), and computed tomography (CT). When CT or MRI imagery, for example, is used, a series of two-dimensional (2D) images are taken from a 3D volume. Each 2D image is an image of a cross-sectional "slice" of the 3D volume. The resulting collection of 2D cross-sectional slices can be combined to create a 3D model or reconstruction of the patient's anatomy (e.g., internal organs). The 3D model will contain organs of interest, which may be referred to as structures of interest herein. Those organs of interest include the organ targeted for radiation therapy (a target), as well as other organs that may be at risk of radiation exposure during treatment. According to some embodiments, the imaging process is a separate process from the treatment planning process, and the treatment planning process can include receiving imaging data from a prior imaging session, for example.

One purpose of the 3D model is the preparation of a radiation treatment plan. To develop a patient-specific radiation treatment plan, information is extracted from the 3D model to determine parameters such as organ shape, organ volume, tumor shape, tumor location in the organ, and the position or orientation of several other structures of interest as they relate to the affected organ and any tumor. The radiation treatment plan can specify, for example, how many radiation beams to use and from which angle each of the beams will be delivered.

In embodiments according to the present invention, the images from the image system 402 are input to a planning system 404. In embodiments, the planning system 404 includes a computing system having a processor, memory, an input device (e.g., a keyboard), and a display. The system 100 of FIG. 1 is an example of a platform for the planning system 404.

Continuing with reference to FIG. 4, the planning system 404 executes software that is capable of producing an optimized treatment plan for treating patient 304. The treatment planning system 404 can receive imagery data generated by image system 402 to determine constraints regarding patient anatomy along with treatment planning parameters, such as other patient-related data and machine parameters. The treatment planning parameters are discretized into spots with defined energy levels, and the spots are sorted according to their depth/energy level. The planning system 404 can optimize the treatment plan according to an optimization algorithm that determines an optimal distribution of layers with a relatively smooth dose distribution. The treatment plan can be optimized in accordance with various prescribed results. For instance, the treatment plan can be optimized to use fewer layers leading to a faster delivery time, or can be optimized for accuracy or 3D dose homogeneity by using more layers to conform to the target volume. The planning system 404 can also receive user input that defines the number of layers used in the optimized plan 408, for example.

The treatment planning system 404 outputs an optimized plan 408 according to an iterative optimizing algorithm 406 as described herein according to embodiments of the present invention. The spots can be distributed at fixed intervals (e.g., 3 mm spacing) or based on variations such as beam energy and/or beam range, and the spots are added to a list of spots that is sorted according to energy level or depth of the spot. Based on the energy levels of the spots and/or the depth/location of a spot, the spots are assigned intensities, where the intensity of a layer is the sum of the intensities of all spots of the layer. The spots are then discretized into blocks according to the energies and intensities, where each block represents a distinct layer. Discretizing the spots into blocks can be an iterative process that is performed repeatedly until a clinical goal or optimization goal is achieved. The optimized plan 408 is then used to configure treatment system 300 for performing proton therapy treatment on patient 304 using gantry 302, for example.

Figure 5:
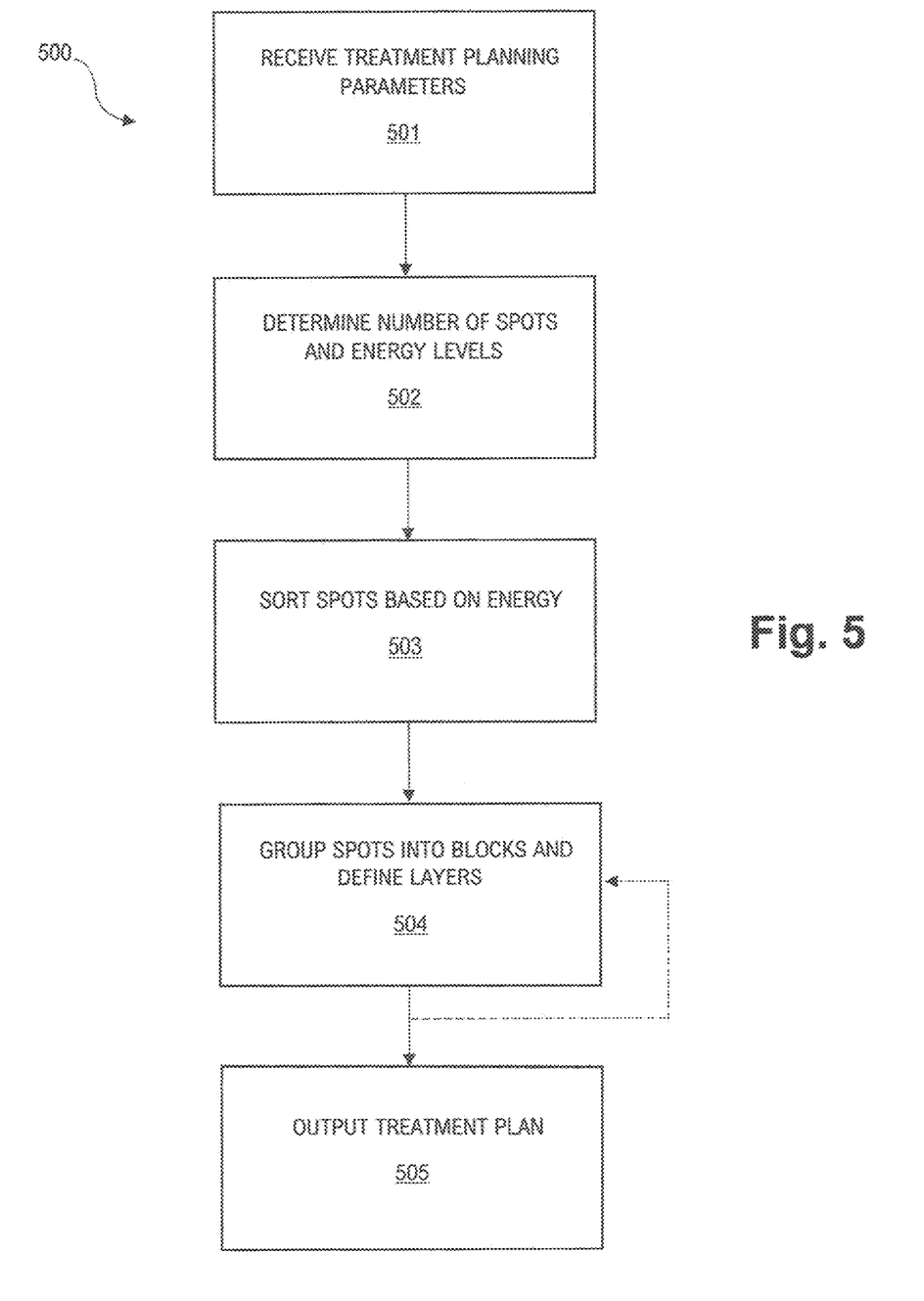
FIG. 5 is a flow-chart depicting an exemplary sequence steps for automatically creating an optimized proton therapy treatment plan according to embodiments of the present invention.

With regard to FIG. 5, an exemplary sequence of computer implemented steps for automatically generating a proton therapy treatment plan is depicted according to embodiments of the present invention. The treatment plan receives treatment planning parameters at step 501, and the parameters may include patient anatomy data and machine parameters. The treatment planning parameters are discretized into spots with defined energy levels at step 502. At this point each spot may have a separate energy level. At step 503, the spots are added to a list of spots and the list is sorted according to energy level or depth of the spot. An optimization algorithm is executed at step 504 to produce an optimal distribution of layer energies and spots with a relatively smooth dose distribution. The spots can be distributed at fixed intervals (e.g., 3 mm spacing) or based on variations such as beam energy and/or beam range, and specifically, the distribution can be based on the energy levels of the spots and/or the depth/location of a spot, the spots are assigned intensities, where the intensity of a layer is the sum of the intensities of all spots of the layer. The spots are then discretized into blocks according to the energies, intensities, and the location of the spots, and each block (705 in FIG. 7) represents a distinct energy layer to be applied by a proton therapy system. Discretizing the spots into blocks can be an iterative process that is performed repeatedly until a clinical goal or optimization goal is achieved.

At step 505, the optimized treatment plan is output, for example, as a computer readable data file. The data file can be stored in memory and used by a proton therapy treatment system to emit a controllable proton beam according to the treatment plan, using a gantry, for example.

According to some embodiments, the optimization algorithm also determines optimal beam angles for a clinical goal or optimization goal and the spots are generated and discretized according to the beam angles.

Figure 6:
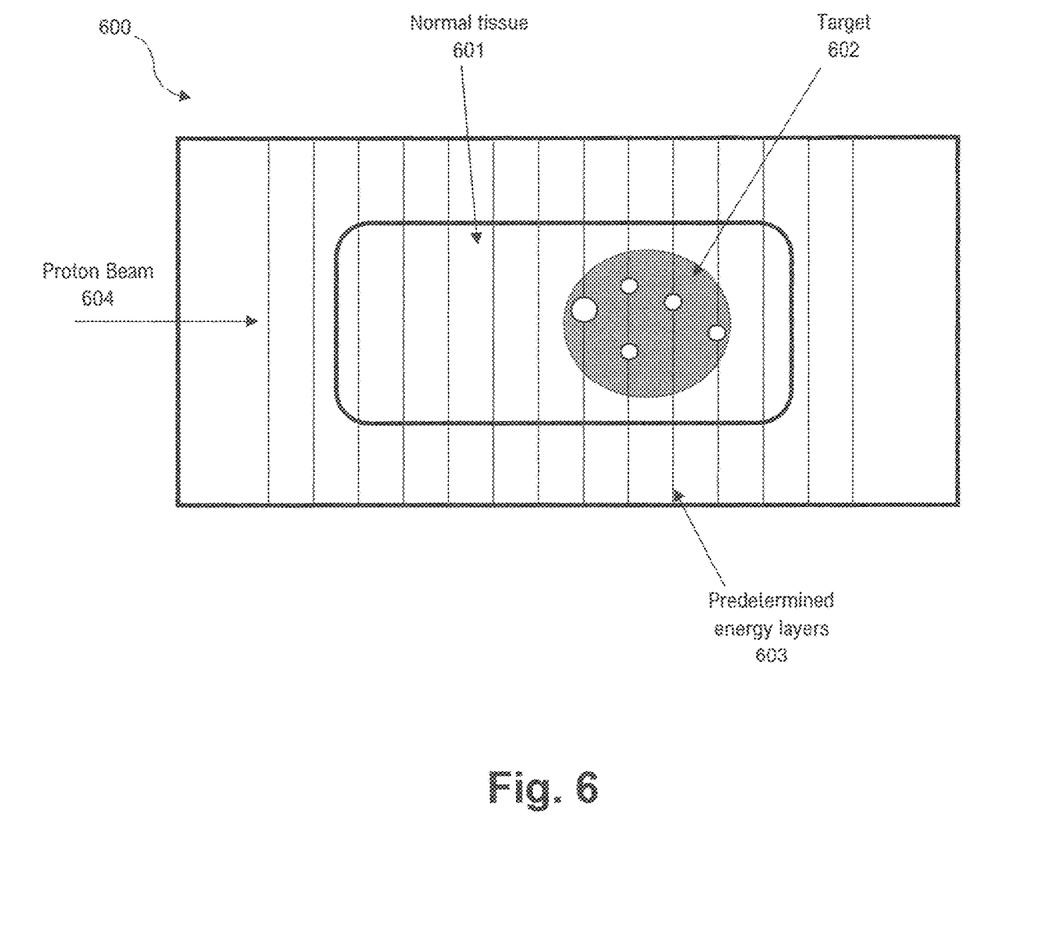
FIG. 6 is a diagram of an exemplary proton therapy treatment plan with predetermined energy layers.

With regard to FIG. 6, an exemplary proton therapy treatment plan 600 applied to a target volume 602 (e.g., a tumor or organ) surrounded by normal tissue 601 for proton therapy treatment is depicted. The treatment plan is generated using limited optimization based on dose volume objectives for the target volume 602 and organs at risk (e.g., normal tissue 601), and machine parameters. Dose distributions are calculated according to the constraints of beam characteristics of proton beam 604 and a machine specific dose calibration. However, the treatment plan depicted in FIG. 6 may not use the full system/machine capability to make use of the system in the most efficient and reliable manner. Moreover, the application of treatment plan 600 at the machine may fail or not achieve the optimal delivery efficiency as requested by plan objectives during treatment planning due to machine specific capability limitations of combined plan parameters that are not taken into account.

As depicted in FIG. 6, the treatment plan is constrained because it is limited to fixed energy layers for discretizing spots produced by proton beam 604 for treating the target volume 602. The energy levels of the predefined layers are defined based on limited considerations of the patient anatomy and characteristics of the treatment device, and a scanning pattern using layers 603 is applied by beam 604 based on these characteristics. Furthermore, using this approach, the deepest layer of the target 602 receives the highest intensity, and layers closer to the surface receive significantly lower intensity, making it difficult to optimize for the surface layers.

Moreover, using the approach depicted in FIG. 6, no less than a certain minimum intensity can be applied to a single spot. Therefore, after optimization, if the intensity of a spot is less than the minimum intensity, the spot must be removed from the plan to generate a plan that is deliverable by the machine. If all spots of an energy layer are below the minimum intensity, the entire layer may need to be removed. A simple removal of spots/layers can change the treatment plan such that the dose distribution is no longer optimal. Moreover, failure to remove these spots or layers from the treatment plan during the planning phase may lead to a failure of the treatment, in which case the treatment must be stopped and restarted after the layer is removed. A more efficient approach involves customizing the number of layers and positioning them as necessary to achieve the clinical objectives, as depicted in FIGS. 7 and 8 below.

Figure 7:
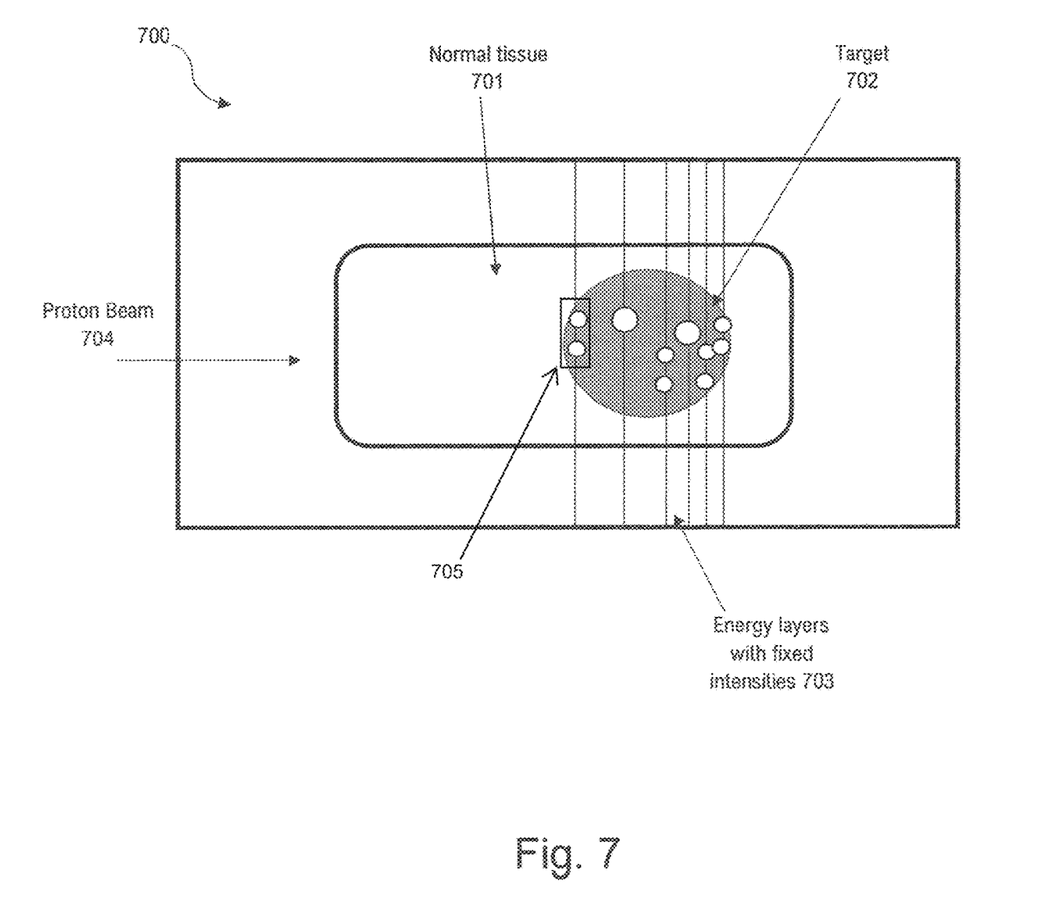
FIG. 7 is a diagram of an exemplary proton therapy treatment plan optimized according to a spot distribution using customized energy layers having a fixed intensity per layer.

With regard to FIG. 7, an exemplary optimized proton therapy treatment plan 700 applied to a target volume 702 (e.g., a tumor or organ) surrounded by normal tissue 701 for proton therapy treatment is depicted. The treatment plan 700 is initially discretized to layers as if there is infinite number of layers, and an iterative optimization process distributes spots using the layers to achieve the clinical goal of treatment plan 700 and ensures that the plan is actually deliverable by the treatment device (e.g., gantry 302). According to some embodiments, an input number of layers is received as user input (for instance). The optimization algorithm then places the spots in a list sorted by range/energy level, and calculates intensities for each spot (e.g., based on energy level/depth) to determine an resultant (e.g., optimal) distribution of layers for achieving the clinical goal of treatment plan 700 using proton beam 704. As depicted in FIG. 7, the treatment plan 700 includes 6 layers 703, and each layer applies ⅙ of the total intensity (number of protons) of treatment plan 700. In this way, the intensities of the layers are fixed, and the spacing of the layers in unconstrained. Splitting the spots among the layers using the principle of equal layer intensities avoids creating spots and layers that are below the minimum intensity deliverable by the treatment system. Note that the principle of equal layer intensities is used here as an example only and other principles could be used to distribute the spots into energy layers. For example, an arbitrary energy-dependent function could be designed to distribute the intensity of the energy layers unevenly. In general, a treatment plan that is optimized using fewer layers leads to a faster delivery time. Moreover, optimizing the treatment plan for accuracy tends to use more layers to better fit the target volume. The spots can be distributed at fixed intervals (e.g., 3 mm spacing) using proton beam 704, or can be distributed based on variations such as beam energy and/or beam range. In either case, the intensity of a layer is the sum of the intensities of all spots on a given layer.

According to some embodiments, the distribution of the layers and/or the energy levels thereof are manually defined by a user. The user-defined energy levels can include layers with an intensity equal to 0 such that no protons are delivered at certain energies, and these layers can be automatically removed by the treatment planning system after the optimization process. The layers can be defined by the user at fixed distances, or custom distances, for example.

Embodiments of the present invention are thus described. While the present invention has been described in particular embodiments, it should be appreciated that the present invention should not be construed as limited by such embodiments, but rather construed according to the following claims.

What is claimed is:

1. A system for proton therapy treatment, the system comprising:
    a gantry including a nozzle configured to emit a controllable proton beam;
    a proton therapy treatment system configured to automatically control the gantry according to a treatment plan; and
    a treatment planning system including
        a memory, and
        a processor configured to
            receive treatment planning parameters,
            determine a quantity of spots, among a plurality of spots, according to the treatment planning parameters,
- determine an energy for each spot, among the plurality of spots, according to the treatment planning parameters,
- calculate intensities for the plurality of spots according to the energy for each spot, among the plurality of spots,
- discretize the plurality of spots into a plurality of blocks according to locations of the plurality of spots and intensities of the plurality of spots to generate the treatment plan, wherein
  - the treatment plan includes the plurality of blocks, and
  - each block, among the plurality of blocks, represents an energy layer, among a number of energy layers, applied by the controllable proton beam, and
- output the treatment plan to the proton therapy treatment system to perform the proton therapy treatment; wherein
- the proton therapy treatment system is configured to automatically control at least one of an intensity, energy, size or shape of the controllable proton beam emitted by the nozzle according to the treatment plan.

2. The system as described in claim 1, wherein the system is configured to treat a patient using the gantry according to the treatment plan.

3. The system as described in claim 1, wherein the processor is configured to iteratively repeat the discretizing of the plurality of spots until a clinical goal is achieved.

4. The system as described in claim 1, wherein the processor is configured to
- determine a plurality of angles for performing the proton therapy treatment, and
- determine the quantity of spots and the energy for each spot according to the treatment planning parameters and the plurality of angles.

5. The system as described in claim 1, wherein the processor is configured to
- receive the number of energy layers as user input, and
- determine the quantity of spots and the energy for each spot according to the treatment planning parameters and the number of energy layers.

6. The system as described in claim 1, wherein the processor is configured to sort the plurality of spots according to depth before discretizing the plurality of spots.

7. The system as described in claim 1, wherein the processor is configured to sort the plurality of spots according to the energy of each spot before discretizing the plurality of spots.

8. The system as described in claim 1, wherein the energy layers are spaced apart from one another by a fixed spacing.

9. The system as described in claim 1, wherein the energy layers have a fixed total intensity.

10. The system of claim 1, wherein each energy layer, among the number of energy layers, has the same intensity as other energy layers among the number of energy layers.

\* \* \* \* \*